United States Patent [19]
Kobayashi

[11] Patent Number: 4,758,782
[45] Date of Patent: Jul. 19, 1988

[54] METHOD AND APPARATUS FOR INSPECTING PRINTED CIRCUIT BOARD

[75] Inventor: Kouji Kobayashi, Ashikaga, Japan

[73] Assignee: Kowa Company Ltd., Aichi, Japan

[21] Appl. No.: 905,922

[22] Filed: Sep. 10, 1986

[30] Foreign Application Priority Data

Sep. 11, 1985 [JP] Japan .................. 60-199588

[51] Int. Cl.$^4$ ............................................ G01R 31/02
[52] U.S. Cl. ................................ 324/73 PC; 358/106
[58] Field of Search .................... 324/73 PC, 73 R; 358/106; 382/8, 16, 34

[56] References Cited

U.S. PATENT DOCUMENTS

| | | | |
|---|---|---|---|
| 3,991,302 | 11/1976 | Danner | 324/73 PC |
| 4,056,716 | 11/1977 | Baxter et al. | 324/73 PC |
| 4,507,605 | 3/1985 | Geisel | 324/73 PC |

OTHER PUBLICATIONS

IEEE Transactions on Pattern Analysis and Machine Intelligence, vol. PAMI-2, No. 1, Jan. 1980, pp. 77-82, article entitled "A Method for Automating the Visual Inspection of PWBs".

*Primary Examiner*—Ernest F. Karlsen
*Attorney, Agent, or Firm*—Bruce L. Adams; Van C. Wilks

[57] ABSTRACT

Method and apparatus for inspecting a printed circuit board wherein scanned image data are digitized and analyzed according to a feature extraction method and a mutual comparison method. The result of both of the analysis methods is combined with predetermined conditions to control output devices including a CRT display or a marking device. The two complementary methods compensate each others drawbacks so that the reliability of inspection can be improved.

5 Claims, 4 Drawing Sheets

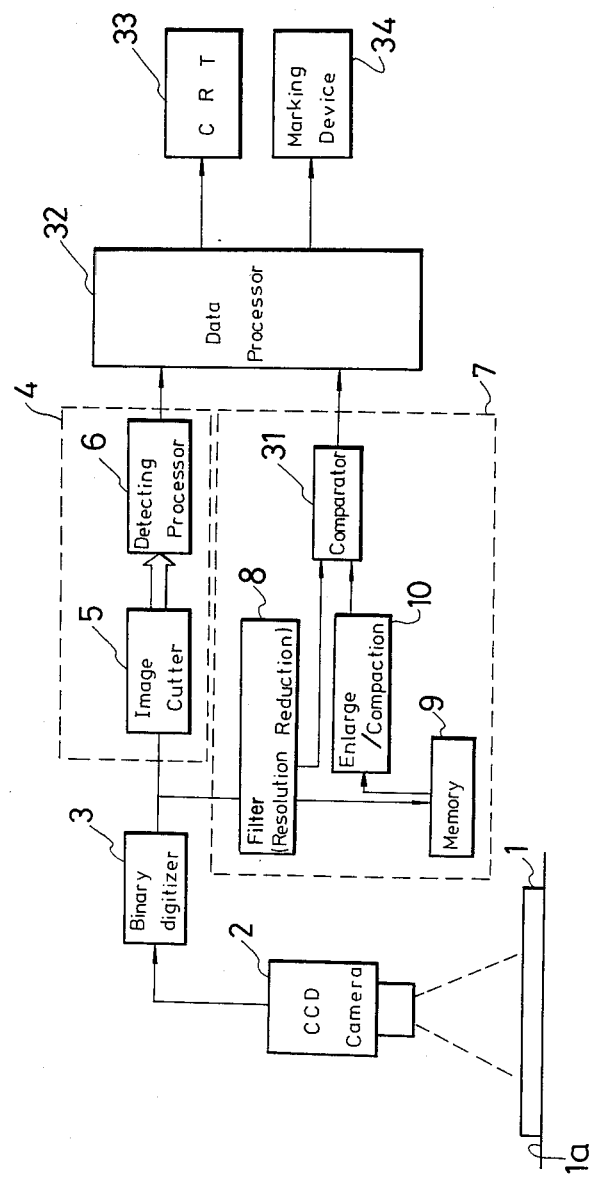

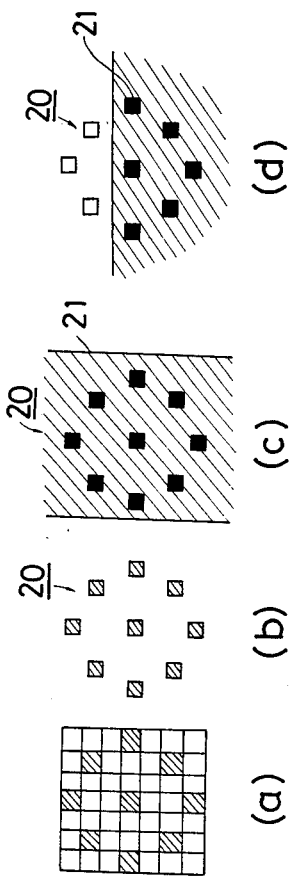
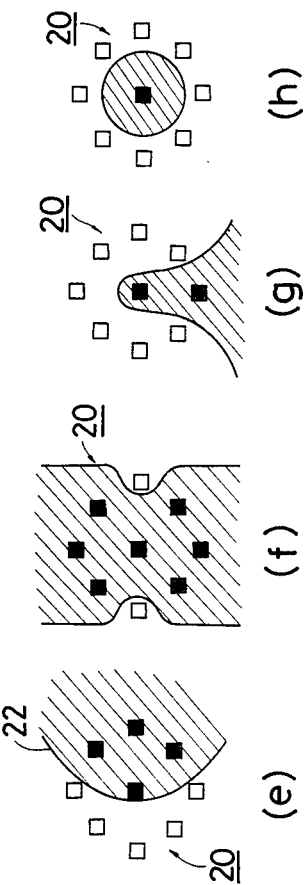
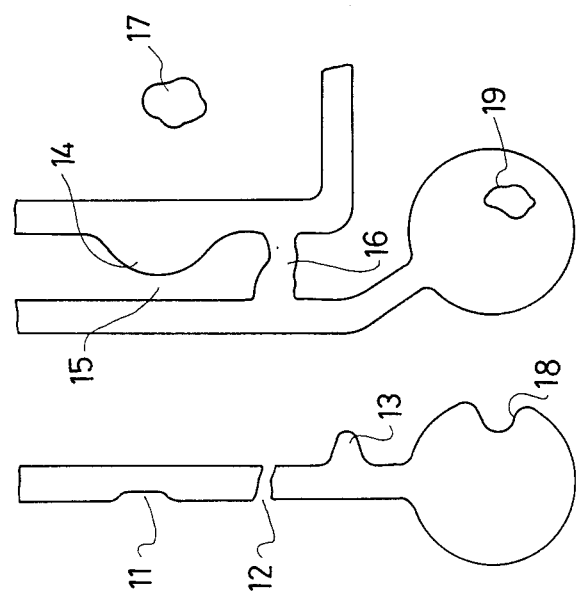

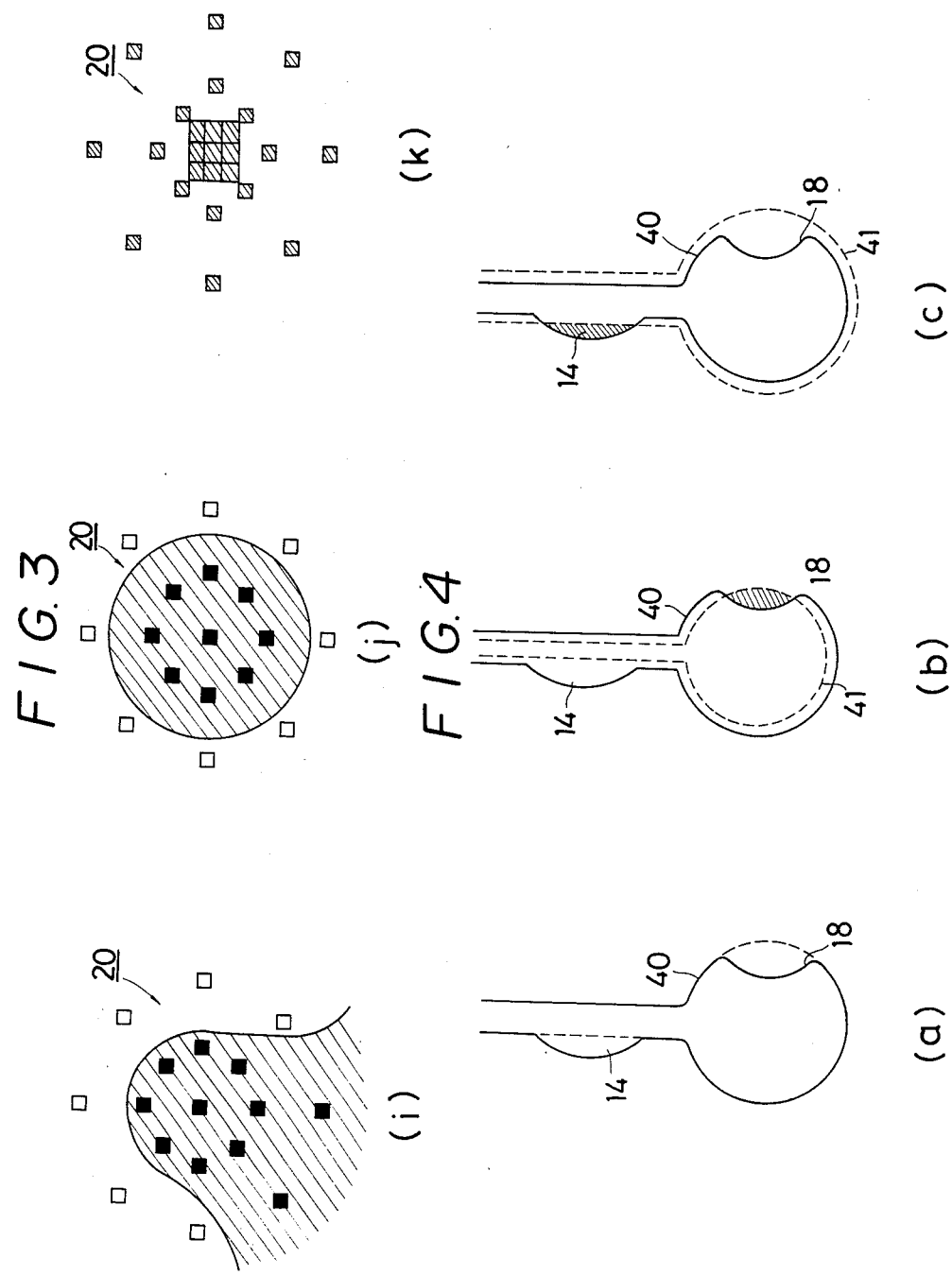

METHOD AND APPARATUS FOR INSPECTING PRINTED CIRCUIT BOARD

BACKGROUND OF THE INVENTION

1. Field of the Invention

This invention relates to method and apparatus for inspecting printed circuit boards, and more particularly to method and apparatus for detecting defective patters on printed circuit boards.

2. Description of the Prior Art

Generally, in production of a printed circuit board, the creation of defective patterns such as cut-offs, short-circuits, irregular thinnesses of projections in the circuit printing step may result in the formation of a defectivce circuit board which causes serious damage to its circuit property if the circuit board is etched without removing those defective patterns therefrom. Nowadays, most circuit boards are inspected via the naked eyes of inspectors before or after the etching step. However, it is inevitable that "naked eye" inspections are occasionaly faulty or uneven because there are human factors such as individual differences between the inspectors, and or fatigue.

There is already in existance an apparatus for automatically inspecting printed circuit boards, whose inspection method can roughly be classified into a mutual comparison method and feature extraction method.

The two methods are generally employed in processing image data scanned by a video camera or CCD line sensor. In the mutual comparison method, defects in the circuit pattern are detected by the logical subtraction of the scanned bit image of the circuit board under inspection from the normal bit image stored in a memory device. On the other hand, in the feature extraction method, the defect is detected by extracting the local image data from the whole scanned image data and analyzing the feature such as the width, the area, or the angle of the pattern under inspection or analyzing whether the pattern have certain characteristics.

The mutual comparison method has the following drawbacks. The method requires such a large capacity memory device that it increases production costs of the inspection system. Although defects in the pattern can be detected without concern of its type or shape, the circuit board to be inspected must be aligned in a predetermined location for accurate inspection. Defective patterns of a smaller size than the order of the board alignment error cannot be detected, and the alignment error sometimes generates a pseudo defect.

On the contrary, the feature extraction method does not have such severe board alignment requirements and has a greater capability of detecting small defects than the mutual comparison method. It is, however, impossible for this method to detect defects which have a similar shape to the normal pattern and which are located at a position where the shape must not exist. However, in the detection of defects having large size according to this method, the image processing becomes complicated, thus requiring a sophisticated image processing system, so that it is very difficult to reduce the price of the apparatus.

SUMMARY OF THE INVENTION

It is therefore an object of the present invention to provide method and apparatus for inspecting printed circuit boards capable of reducing the production cost.

It is a another object of the present invention to provide method and apparatus for inspecting printed circuits boards which will allow the reliable detection of defects in the printed circuit pattern.

In the present invention, both the feature extraction method and the mutual comparison method are employed. The image data of the printed circuit board under inspection is scanned, digitized and entered independently into the feature extraction process and the mutual comparison process. In the feature extraction process, local image data extracted from the digitized image data are examined to detect the pattern defects, while, in the mutual comparison process, the image data of the circuit board are compared with the image data scanned, digitized and stored prior to the inspection. The results from the two methods are combined to control certain output devices for displaying or marking the detected printed pattern defect.

According to one feature of the present invention, it is possible to improve the reliability of defect detection. The two complementary analysis methods compensate each other's drawbacks. Further, it is possible to detect defects including defective patterns having similar shape to the normal pattern and of smaller size than the order of board alignment error, or patterns located at a position where the pattern should not exist. Further, it is possible to reduce the pseudo defect detection due to the deviation of the board alignment.

According to another feature of the present invention, the resolution of the image data of the normal circuit pattern and the pattern to be inspected are reduced prior to the comparison in the mutual comparison process.

According to other features of the present invention, the memory capacity required for the storage of the image data of the normal circuit pattern or the pattern to be inspected is reduced, so that it is possible to reduce the production costs of the inspection apparatus.

BRIEF DESCRIPTION OF THE DRAWINGS

The objects and features of the present invention will become more apparent from a consideration of the following detailed description taken in conjunction with the accompanying drawings, in which:

FIG. 1 is a block diagram showing the configuration of an apparatus for inspecting printed circuit board according to the present invention;

FIG. 2 is an explanatory drawing illustrating defective patterns which may appear on a printed circuit board;

FIGS. 3a to 3k are explanatory drawings illustrating the feature extraction method used in the present invention;

FIGS. 4a to 4c are explanatory drawings illustrating the mutual comparison method used in the present invention.

DETAILED DESCRIPTION OF PREFERRED EMBODIMENTS

Figure 5:
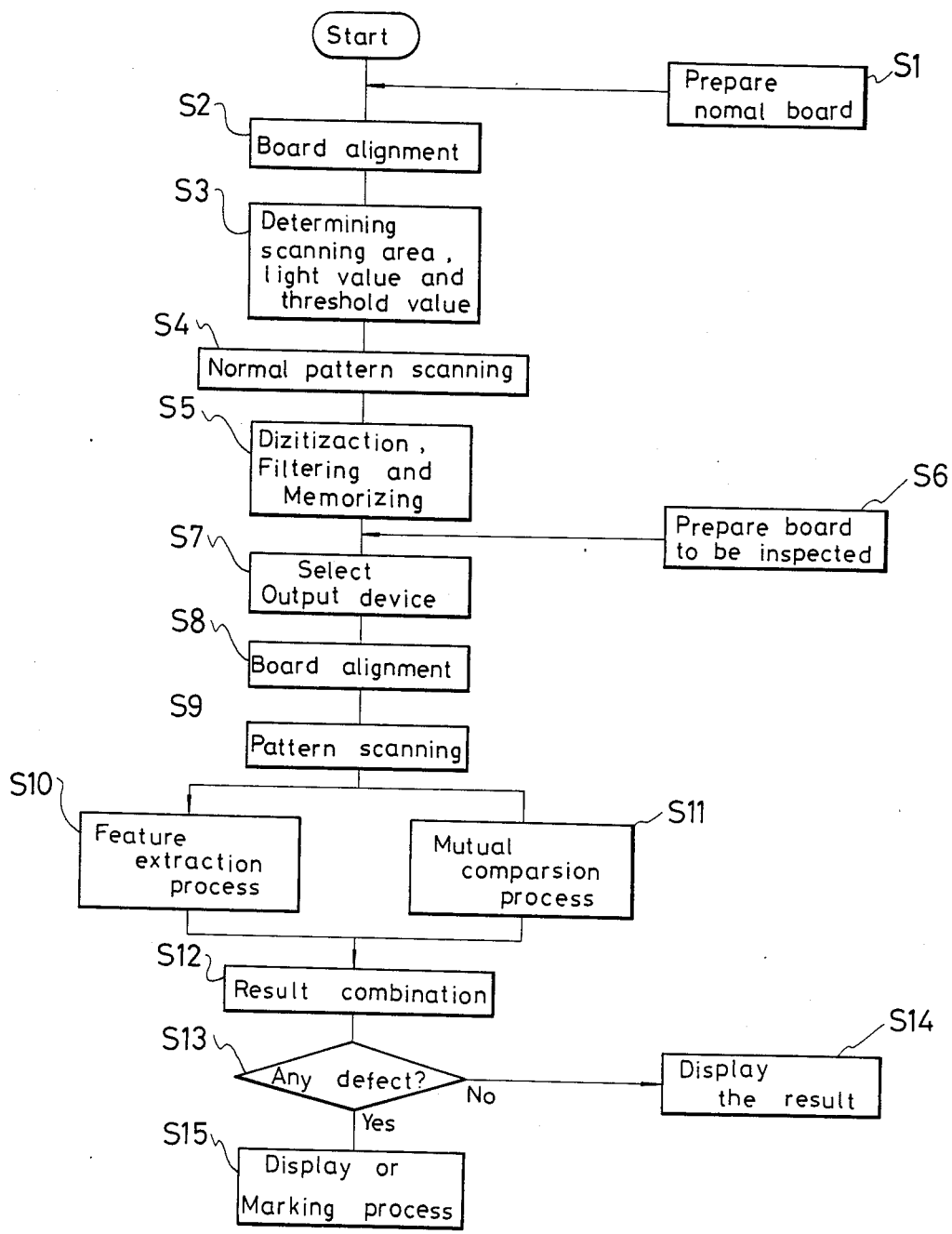
FIG. 5 is a flow chart illustrating the operation and processing procedure in the apparatus as shown in FIG. 1.

FIG. 1 is a block diagram showing a preferred embodiment of an inspection apparatus in accordance with this invention. In FIG. 1, reference numeral 2 denotes a CCD video camera for scanning a printed pattern on an printed circuit board 1, which is disposed on a table 1a for inspection prior to ( or after ) the etching process.

The printed pattern is scanned as the camera 2 or the circuit board 1 moves. The camera 2 may be constructed as a two-dimensional photosensor for scanning two-dimensional image data.

The scanned image data from the camera 2 are converted into a black-and-white binary digital data by a binary digitizer 3 and then fed to two image data processors, which are a feature extraction processor 4 and a mutual comparison processor 7. In this embodiment, defects in the printed pattern are thus detected using the two processors by the feature extraction method as well as the mutual comparison method.

FIG. 2 shows typical defects 11 to 19 on the printed pattern, which are respectively an irregular thinness, a cutoff, a projection, a swelling of the pattern, an irregular vicinity of the patterns caused by the projection or the swelling, a short-circuit, a dot point isolated from the virtual pattern, a missing point or a pinhole in the pattern etc. The defects 11 to 19, whose sizes or dimensions are smaller than the positioning error of the circuit board 1, are detected by the feature extraction processor 4, while the defects of greater size or dimension than the positioning error are detected by the mutual comparison processor 7.

The detection output signals generated by the image data processors 4 and 7 are entered to a data processor 32. The data processor 32 is comprised of a processing circuit such as a microprocessor, and controls a CRT display 33 to display thereon the detected defective patterns or their coordinates, as well as a marking device 34 to mark the defect pattern on the circuit board 1. The processor 32 controls the display 33 and/or the marking device 34 by combining the output detection signals from the two image processors 4, 7 with predetermined logical criteria such as OR or AND condition.

The feature extraction processor 4 is structured as described below. The binary image data generated by the digitizer 3 are entered into a local image cutter 5 composed of shift registers. The image cutter 5 divides the scanned image comprised of a plurality of digitized image elements into a plurality of localized two-dimensional image segments each having a row-and-column matrix configuration in the form of a 7×7 picture or image element configuration as shown in FIG. 3a. Then the central 1 bit of image element and the peripheral circular or equi-angularly disposed 8 bits of image elements are extracted or selected as shown in FIG. 3b, and the extracted 9 bit image 20 is fed to a detecting processor 6.

The whole width of the 7×7 configuration of the picture elements is a little narrower than that of a lead (straight portion of the printed pattern) 21. The sum of the possible combination of the extracted or selected 9 bit black and white images is 512 ($=2^9$). All of the combinations can be divided into two categories or groups. One is composed of the bit patterns that may appear in the scanning of the normal circuit pattern and that indicate an absence of a pattern defect, and the other is composed of the bit patterns that must not appear in the normal circuit pattern and that indicate a presence of a pattern defect.

Accordingly, in this embodiment, a ROM is employed for the detecting processor 6 and the extracted 9 bit signal 20 is fed as an address input of the ROM, whose memory cell has '1' (normal) or '0' (defective) data or memory content corresponding to the its address input.

Even though the criteria that determines whether a pattern is normal or defective is different corresponding to the characteristics of the scanned pattern, the patterns are regarded as normal or defective as described below.

If the lead 21 is scanned as shown in FIG. 3c, the extracted 9 bit image data 20 are all black. The black and white patterns of the image data 20 shown in FIGS. 3d and 3e are allowed to appear when the camera 2 scans a border area of the lead 21 or a land 22.

On the other hand, FIGS. 3f, 3g and 3h show black and white patterns of extracted image data 20, which must not appear in the scanning of the normal printed pattern. FIGS. 3f to 3h show a black and white pattern extracted respectively from a irregular thinness (or vicinity) of the circuit pattern, from an irregular projection (or losing) of the circuit pattern and from an isolated pattern (or a pinhole). The above description in the parentheses denotes the defects which appear when the black and white bit pattern is reversed.

Thus, the circuit board can be inspected by reading out the memory content of the detecting processor (ROM) 6 in synchronism with the scanning of the circuit patterns. The experimental inspection showed that 70% of the defects can be detected using only the 9 bit image extraction method shown above.

In this embodiment, the detection processor 6 can be structured in a simple configuration, employing a ROM having at least 512 bits capacity, so that the production cost can be reduced, and the defect detection can be made with very simple programming which in turn enables very fast processing speed.

Various alternative arrangements may be made for the feature extraction processor 4. For example, 8 bits of outer picture or image elements can be added around the 9 bits of inner image elements as the input image data as shown in FIGS. 3i, 3j, in order to increase the detection area. FIGS. 3i and 3j respectively show the detection of the large projection and isolated pattern. The detection area can be increased to as broad as a 25 bit area as shown in FIG. 3k.

Most of the relatively small defective patterns on the circuit board can be detected using the feature extraction method without any pseudo defect detection.

The mutual comparison processor 7 is constructed as described below.

Generally in the mutual comparison method, all of the scanned image data are memorized and the scanned image is compared with the stored image data of the normal or master pattern.

However, if a picture element taken by the CCD of the camera 2 corresponds to a 30×30 micron area, the memory capacity required for the storage of the 500×500 mm board image becomes as great as 32 megabytes ($=500\times 10^3/30)^2$.

In this embodiment, the resolution of the stored normal image data and scanned image data is reduced by a filter 8, in order to make the memory capacity requirement smaller. The filter 8 reduces the resolution of both sample and master pattern image data, for example, to ½ of the resolution of the CCD of the camera 2 with respect to the length of the CCD (to ¼ with respect to the area of the CCD).

With this resolution reduction, the memory capacity for normal image data can be reduced to ¼. In the above referred instance, the 32 megabyte memory capacity requirement can be reduced to 8 megabytes.

The scanned binary image data from the digitizer 3, with their resolution low-resolution reduced by the filter 8 are compared (subtracted) by the comparator 31 with the normal image data prepared in the memory 9. The normal image data fed into the comparator 31 are enlarged or compacted by the scale changing circuit 10.

The purpose of the scale change is to reduce the pseudo defect detection, which often occurs under the condition that the circuit board 1 is disposed with some alignment error.

Assume that the printed pattern 40 under inspection has a projected portion 14, or a lost portion 18 as shown in FIG. 4a. The lost or indent portion 18 can be detected if the normal image data are compacted or similarly reduced as shown in FIG. 4b, while the projected portion 14 can be detected if the normal image data is enlarged as shown in FIG. 4c. If the scanned image data are compared both with the enlarged and the compacted pattern, both of the projected and lost portions can be detected.

With the change of the scale, up to 100 microns of alignment error of the circuit board 1 can be allowed, where 1 bit data of the memory 9 correspond to the 60×60 micron picture element.

The results of the feature extraction and the mutual comparison are combined as described below.

FIG. 5 is a flow chart showing procedures of the operator and the image data processing of the apparatus.

First of all, in step S1 of FIG. 5, a printed circuit board having normal printed pattern is mounted on the inspection table 1a. The normal circuit board is inspected via naked eyes of the inspector prior to this step. In step S2, the board is brought into alignment with the determined position using a positioning device such as a guide plate or grooves.

In step S3, the scanning conditions including the scanning area of the camera 2, the illumination light value or the threshold value of the binary digitizer 3 are determined. The light value and the threshold value are determined by a conventional method using a reference white surface.

The image data of the normal pattern are scanned in step S4, digitized by the digitizer 3, reduced in resolution and then stored in the memory 9 in step S5.

In step S6, the circuit board with the normal pattern on the table 1a is substituted with a sample board to be inspected.

In step S7, it is determined how the inspection result should be utilized. The result output using the CRT display 33 or marking device 34 can be selected via an input device such as a keyboard (not shown in the drawings). In the illustrated embodiment, the coordinates of the defect can be displayed on the CRT display 33, or the defect can be marked by the marking device 34.

In step S8, the circuit board (in the pre- or post-etching process) is brought into alignment with the determined position, and scanned by the camera 2 with the same scanning condition utilized in the scanning of the normal board.

In steps S10 and S11, the scanned and digitized image data are entered into image processors 4 and 7, where both the feature extraction process and the mutual comparison process are simultaneously carried out.

The results of the feature extraction and the mutual comparison are entered into the data processor 32, and combined with a certain logical condition such as OR or AND in step S12. The processor 32 converts the combined result into the acceptable data by the CRT display 33 or the marking device 34.

In step S13, the processor 32 judges whether a defect exists or not. In case of no defect, the result is displayed on the CRT display in step S14. If some defect is detected, the result is fed to the display 33 or the marking device 34 according to the selection made in step S7.

Thus, in the illustrated embodiment, both the feature extraction and the mutual comparison method are employed, so that it is possible to detect the defects, including defects having a certain shape or size smaller than the order of the board alignment error, which could not be detected in conventional apparatus using only one of the detection methods. The filter and the scale changing circuit solve, respectively the two major drawbacks of the mutual comparison method namely, the large capacity memory requirement and the detection of pseudo defects caused by alignment error. The combination of the two methods allows the detection of defects having an indetectable shape.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

I claim:

1. An apparatus for inspecting printed circuit boards to detect defective printed circuit patterns formed thereon, comprising:
   a. image scanning means for scanning a printed circuit pattern of said printed circuit board to produce a pattern image in the form of a plurality of image data;
   b. binary digitizing means for digitizing the image data of said printed circuit pattern to produce a plurality of corresponding binary image data;
   c. first inspection processing means including,
      extracting means for extracting local binary image data composed of a central bit image and peripheral bit images having a pre-determined bit configuration and being spaced apart from each other, from the binary image data generated by said binary digitizing means, and
      detection means composed of a memory device for receiving said extracted local binary image data as an address input and outputting stored data indicating whether a defect exists or not in a pattern area from which said local binary image data is extracted;
   d. second inspection processing means including,
      converting means for converting the binary image data generated by said binary digitizing means into binary image data of lower resolution than that of the binary image data entered into said first detection means,
      image data storage means for storing resolution-lowered binary image data of a master printed circuit board, which are scanned, digitized and converted in terms of the resolution by said scanning means, digitizing means and converting means, enlarging and reducing means for enlarging and reducing the resolution-lowered binary image data of the master printed circuit board read out from said image data storage means, and detection means for detecting defects of the printed circuit board to be inspected, by comparing the image data of the printed circuit board whose resolution is lowered by said converting means, with the enlarged and reduced master image data produced by said enlarged and reducing means; and e. output processing means for combining detection results from said first and second detection means to produce output data which can be utilized in a predetermined output device.

2. An apparatus according to claim 1; wherein said extracting means includes means for extracting local binary image data composed of a central bit image surrounded by peripheral bit images having a circular configuration.

3. An apparatus according to claim 1; wherein said extracting means includes means for extracting local binary image data composed of a central bit image surrounded by peripheral bit images equi-angularly positioned around the central bit image.

4. An apparatus according to claim 1; wherein the enlarging and reducing means includes means for producing an enlarged similar image effective to enable the detection means to detect a projection defect of the sample pattern.

5. An apparatus according to claim 1; wherein the enlarging and reducing means includes means for producing a reduced similar image effective to enable the detection means to detect an indent defect of the sample pattern.

* * * * *